United States Patent
Niu et al.

(10) Patent No.: US 7,072,049 B2
(45) Date of Patent: Jul. 4, 2006

(54) MODEL OPTIMIZATION FOR STRUCTURES WITH ADDITIONAL MATERIALS

(75) Inventors: Xinhui Niu, Los Altos, CA (US); Nickhil Jakatdar, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 326 days.

(21) Appl. No.: 10/357,705

(22) Filed: Feb. 3, 2003

(65) Prior Publication Data

US 2004/0150838 A1 Aug. 5, 2004

(51) Int. Cl.
*G01B 11/24* (2006.01)
(52) U.S. Cl. .................... 356/601; 356/237.5; 356/625
(58) Field of Classification Search ............. 356/237.5, 356/625, 601, 636
See application file for complete search history.

(56) References Cited

U.S. PATENT DOCUMENTS

| | | | | |
|---|---|---|---|---|
| 6,608,690 B1 * | 8/2003 | Niu et al. | ................. | 356/635 |
| 6,768,983 B1 * | 7/2004 | Jakatdar et al. | ............... | 706/46 |
| 2002/0035455 A1 | 3/2002 | Niu et al. | | |
| 2002/0113966 A1 * | 8/2002 | Shchegrov et al. | ......... | 356/369 |
| 2003/0058443 A1 | 3/2003 | Xu et al. | | |
| 2003/0187604 A1 | 10/2003 | Drege et al. | | |

FOREIGN PATENT DOCUMENTS

WO    WO 03/068889 A1    8/2003

OTHER PUBLICATIONS

UK Search Report mailed on Jul. 21, 2004, for UK patent application No. GB 0402260.4 filed on Feb. 2, 2004, 2 pages.

* cited by examiner

*Primary Examiner*—Richard A. Rosenberger
(74) *Attorney, Agent, or Firm*—Morrison &Foerster LLP

(57) ABSTRACT

A wafer structure profile is modeled by determining one or more termination criteria. A determination is made as to whether a wafer structure includes at least one layer having three or more materials alone a line within the at least one layer. An optical metrology model for the wafer structure is created, where three or more materials are incorporated in the model for the at least one layer having three or more materials. A set of diffraction signals is simulated using the optical metrology model. The set of simulated diffraction signals and a set of diffraction signals measured off of the wafer structure are used to determine if the one or more termination criteria are met. The optical metrology model is modified until the one or more termination criteria are met.

32 Claims, 7 Drawing Sheets

MODEL OPTIMIZATION FOR STRUCTURES WITH ADDITIONAL MATERIALS

CROSS REFERENCE TO RELATED APPLICATIONS

This application relates to co-pending U.S. patent application Ser. No. 09/727,530, entitled "System and Method for Real-Time Library Generation of Grating Profiles" by Jakatdar, et al., filed on Nov. 28, 2000; to co-pending U.S. patent application Ser. No. 10/206,491, entitled "Model and Parameter Selection in Optical Metrology" by Voung, et al., filed on Jul. 25, 2002; and to co-pending U.S. patent application Ser. No. 10/007,124, entitled "Optical Profilometry of Additional Material Deviations in a Periodic Grating", by Niu, et al., filed on Dec. 4, 2001.

BACKGROUND

1. Field of the Invention

The invention relates to integrated circuit (IC) metrology and more particularly to a method and system for optimizing wafer structure profile modeling.

2. Related Art

Growing demand for silicon wafers with large-scale integration necessitates submicron integrated circuit (IC) features with high precision and uniformity. As the features become smaller, it is increasingly critical to monitor the photolithographic process under which such semiconductor wafers are created.

In a typical photolithographic process, the silicon wafers undergo a number of doping and layering steps. In addition, a series of masks are applied to the wafers at each layer whereby the masks are used to transfer circuitry patterns onto photosensitive layers (i.e., a photoresist layer) that are coated onto the layers (e.g., metal layer, etc.) formed on the silicon wafer. However, the steps under which a wafer is processed contain some deviations from perfect calibration, thereby resulting in some variations on the wafer's surface.

As feature sizes shrink, techniques for measuring wafer structure profiles and critical dimension (CD) are crucial to higher yield and device performance. The wafers are monitored to ensure the measurements of critical dimension (CD) of the wafer structures are within that set by a design rule. The design rule regulates features such as the minimum width of a line or the minimum spacing between two lines in order to ensure that the lines do not overlap or unintentionally interact.

One technique for monitoring a silicon wafer is to create a profile model of the target structures on a silicon wafer, the modeled profile measurements are then compared to actual measurements of the target structures on the wafer in order to detect any variation on the wafer.

Conventional methods model the profile of a wafer structure as if each layer of a wafer is composed of no more than two distinct materials such as a combination of silicon dioxide and atmospheric gas. The resulting profile models do not take into account the difference in the diffraction signals caused by the presence of three or more materials in a layer.

SUMMARY

In one exemplary embodiment, a wafer structure profile is modeled by determining one or more termination criteria. A determination is made as to whether a wafer structure includes at least one layer having three or more materials alone a line within the at least one layer. An optical metrology model for the wafer structure is created, where three or more materials are incorporated in the model for the at least one layer having three or more materials. A set of diffraction signals is simulated using the optical metrology model. The set of simulated diffraction signals and a set of diffraction signals measured off of the wafer structure are used to determine if the one or more termination criteria are met. The optical metrology model is modified until the one or more termination criteria are met.

DESCRIPTION OF DRAWING FIGURES

The present invention can be best understood by reference to the following description taken in conjunction with the accompanying drawing figures, in which like parts may be referred to by like numerals:

DETAILED DESCRIPTION

The following description is presented to enable one of ordinary skill in the art to make and use the invention and is provided in the context of a patent application and its requirements. In the following description, specific nomenclature is set forth to provide a thorough understanding of the present invention. It will be apparent to one skilled in the art that the specific details may not be necessary to practice the present invention. Furthermore, various modifications to the embodiments will be readily apparent to those skilled in the art and the generic principles herein may be applied to other embodiments. Thus, the present invention is not intended to be limited to the embodiments shown but is to be accorded the widest scope consistent with the principles and features described herein.

In order to facilitate the description of the present invention, an ellipsometric optical metrology system is used to illustrate the concepts and principles. It is understood that the same concepts and principles equally apply to the other IC optical metrology systems such as reflectometric systems and the like.

Figure 1:
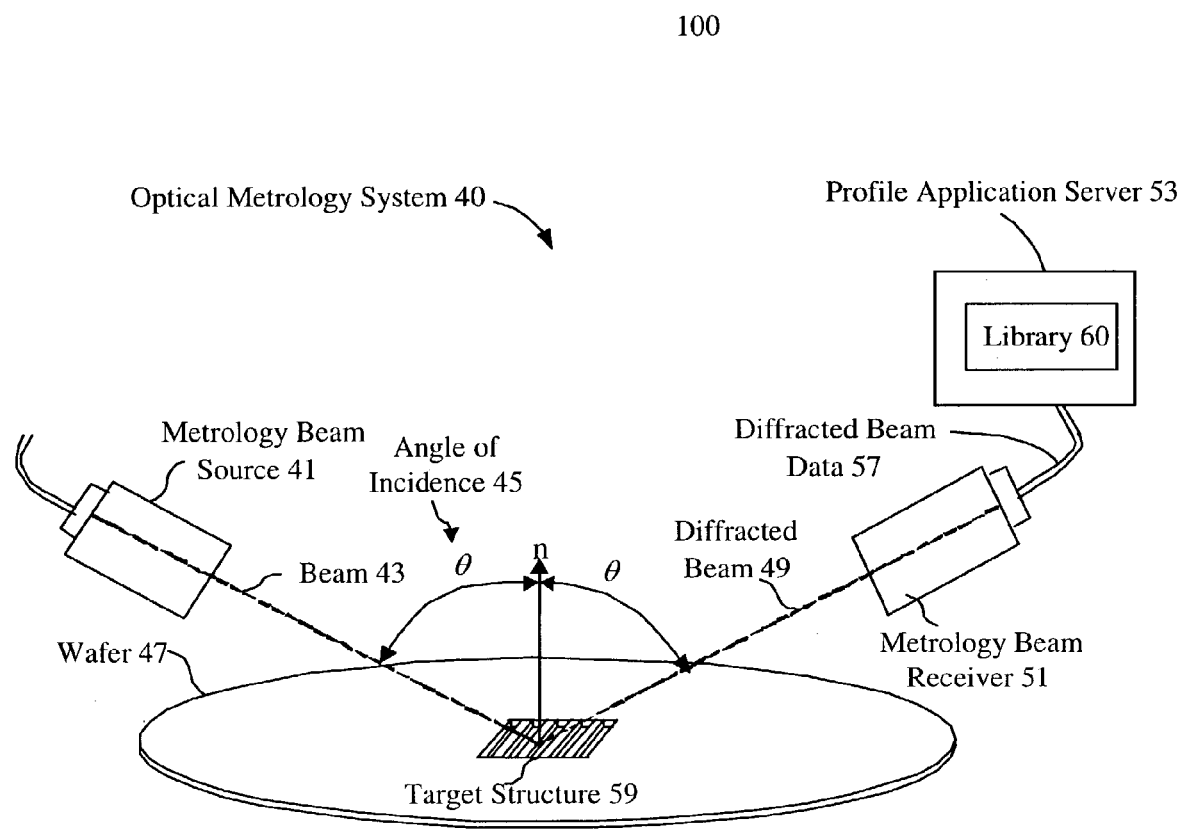
FIG. 1 is an architectural diagram illustrating an exemplary embodiment where an optical metrology device can be utilized to determine the profiles of structures on a semiconductor wafer.

FIG. 1 is an architectural diagram 100 illustrating an exemplary embodiment where optical metrology can be utilized to determine the profiles of structures on a semiconductor wafer. The optical metrology system 40 includes a metrology beam source 41 projecting a beam 43 at the target structure 59 of a wafer 47. The metrology beam 43 is projected at an incidence angle θ towards the target structure 59. The diffraction beam 49 is measured by a metrology beam receiver 51. The diffraction beam data 57 is transmitted to a profile application server 53. The profile application server 53 compares the measured diffraction beam data 57 against a library 60 of calculated diffraction beam data representing varying combinations of critical dimensions of the target structure and resolution. In one exemplary embodiment, the library 60 instance best matching the measured diffraction beam data 57 is selected. It is understood that although a library of diffraction signals and associated profiles is frequently used to illustrate concepts and principles, the present invention equally applies to a data space comprising simulated diffraction signals and associated set of profile parameters, such as in regression, neural net, and similar methods used for profile extraction. The profile and associated critical dimensions of the selected library 60 instance correspond to the cross-sectional profile and critical dimensions of the features of the target structure 59. The optical metrology system 40 may utilize a reflectometer, an ellipsometer, or other optical metrology device to measure the diffraction beam or signal. An optical metrology system is described in co-pending U.S. patent application Ser. No. 09/727,530 entitled "System and Method for Real-Time Library Generation of Grating Profiles" by Jakatdar, et al., filed on Nov. 28, 2000, and is incorporated in its entirety herein by reference.

Moreover, the optical metrology system 40 inspects wafer 47 by measuring several sample points on the wafer. Normally, both the overall inspection time and the accuracy of the inspection increase with an increasing number of sample points, and therefore the number of sample points under inspection is generally adjusted according to desired maximum inspection time and required minimum accuracy, although a minimum number of sample points may be set to ensure the adequacy of the resulting data set.

Figure 2:
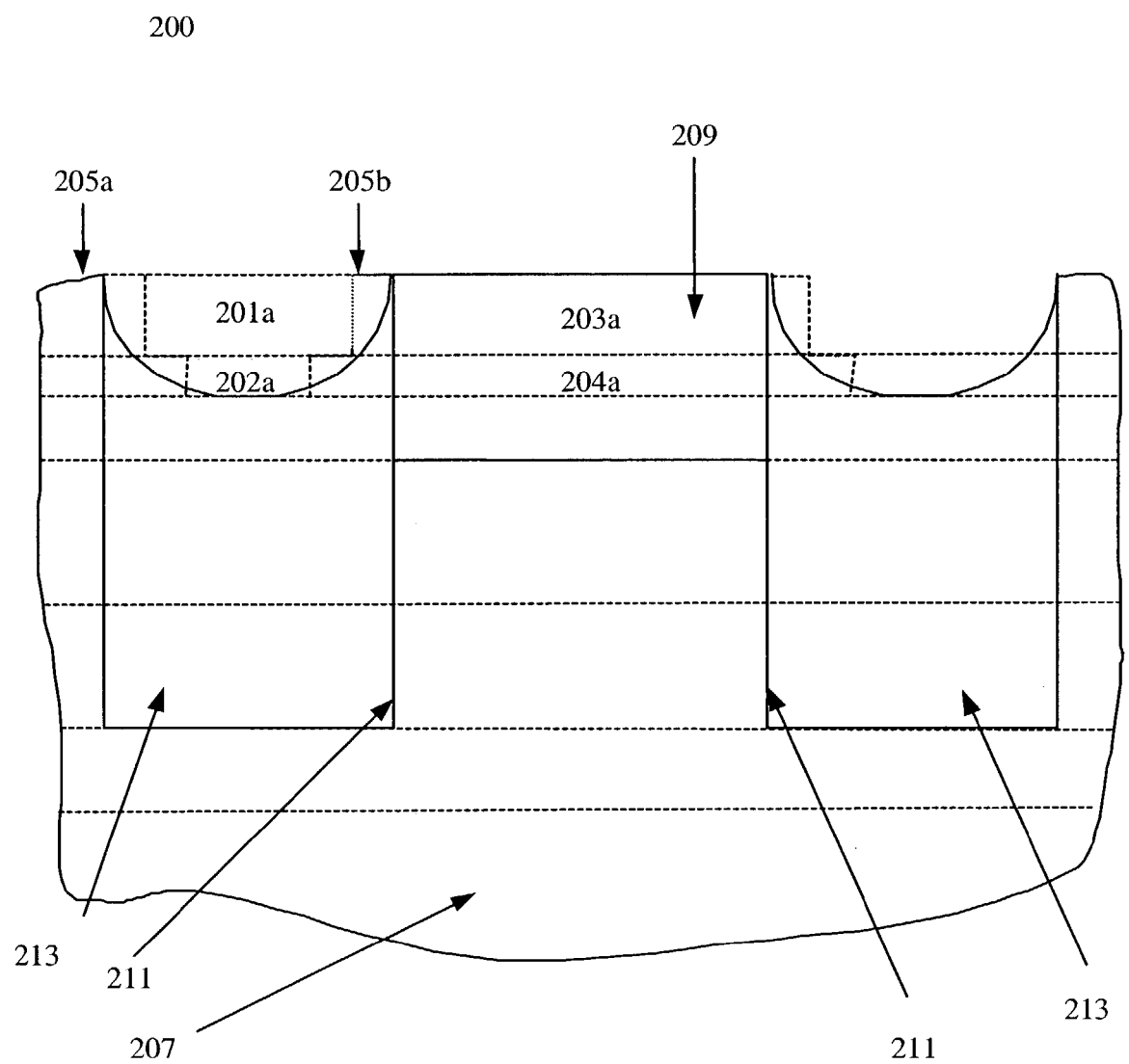
FIG. 2 is a profile diagram illustrating an exemplary embodiment wherein a top layer of a periodic structure comprises three distinct materials along a line of periodicity.

FIG. 2 is a profile diagram 200 illustrating an exemplary embodiment wherein a top layer of a periodic structure having more than two distinct materials along a line of periodicity. Diagram 200 illustrates a periodic structure that underwent a chemical mechanical polishing (CMP) process. The periodic structure includes a substrate 207 with a nitride layer 209 formed thereon. As shown in FIG. 2, troughs 211 are etched in a periodic manner in the substrate 207 and nitride layer 209. Silicon dioxide plugs 213 are then placed in troughs 211. Since silicon dioxide is softer than nitride, when the CMP process is applied to the periodic structure, silicon dioxide plugs 213 will erode further than nitride layer 209. This further results in portions of silicon dioxide plugs 213 to dip below the top surface of the nitride layer 209.

In particular, near the top surface of the nitride layer 209, the semiconductor device has three materials occurring along a line parallel to the periodic direction: nitride, silicon dioxide, and atmospheric gas. Specifically, slabs 201a and 202a comprise atmospheric gas; slabs 203a and 204a comprise nitride; and slabs 205a and 205b comprise silicon nitride.

FIG. 2 is an exemplary embodiment wherein a top layer of a periodic structure comprises three distinct materials. As noted earlier, in conventional methods, a profile of a wafer structure is modeled as having no more than two distinct material. Therefore, as will be described in greater detail below, in order to create a profile model for the periodic structure shown in FIG. 2, one additional material (in this example, three distinct materials) are incorporated.

Figure 3:
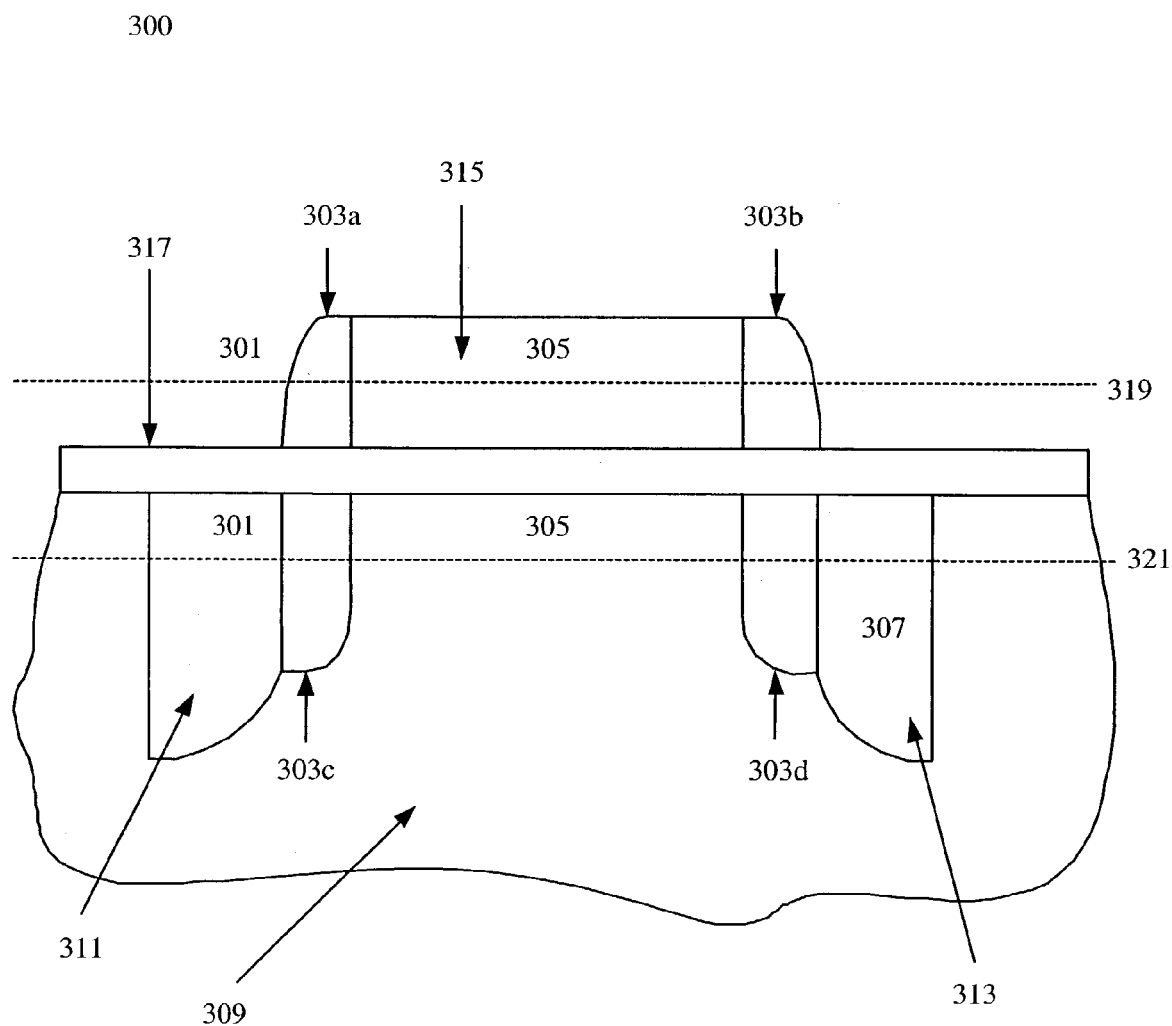
FIG. 3 is a profile diagram illustrating an exemplary embodiment wherein a field effect transistor having a top layer comprising three distinct materials along a first line and a bottom layer comprising four distinct materials along a second line.

FIG. 3 is a profile diagram 300 illustrating an exemplary embodiment wherein a field effect transistor having a top layer comprising three distinct materials and a bottom layer comprising four distinct materials. The field effect transistor includes a source 311, a drain 313, and a gate 315. The gate 315 is placed on top of an insulating oxide barrier layer 317 that coats a substrate 309. A top left spacer 303a is formed on the left side of gate 315 above barrier layer 317; a top right spacer 303b is formed on the right side of gate 315 above barrier layer 317; a bottom left spacer 303c is formed on the left side of gate 315 below barrier layer 317; a bottom right spacer 303d is formed on the right side of gate 315 below barrier layer 317.

Moreover, three distinct materials lie along a line 319 in a layer of the field effect transistor: atmospheric gas 301, the material of top spacers 303a and 303b, and the material of gate 315. Similarly, four materials lie along a line 321: the material of substrate 309, the material of lower spacers 303c and 303d, the material of source 311, and the material of drain 313.

FIG. 3 is an exemplary embodiment wherein a layer of a transistor comprises three distinct materials along a first line of periodicity. Therefore, in order to create a profile model along the first line, one additional material (in this example, a total of three distinct materials) is incorporated in the layout. Moreover, the transistor in FIG. 3 comprises four distinct materials along a second line, and two additional materials (in this example, a total of four distinct materials) are incorporated to create a profile model along the second line.

Figure 4A:
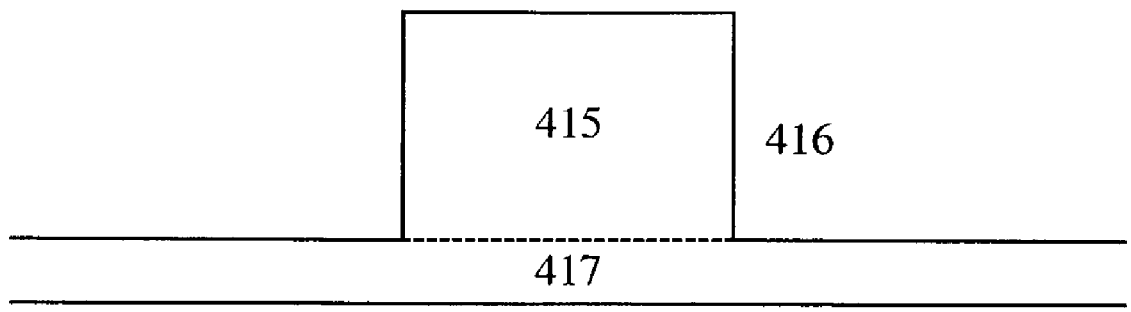
FIG. 4A is profile model of a wafer structure comprising atmospheric gas and a nitride material, in accordance to one exemplary embodiment of the present invention.

FIG. 4A illustrates a profile model of a wafer structure comprising two distinct materials of atmospheric gas and nitride. This is an example where the profile model includes a structure made of one material 415, a nitride material, and an underlying film 417. Along the line of periodicity of the structure, there are two materials consisting of the nitride material 415 and atmospheric gas 416.

Figure 4B:
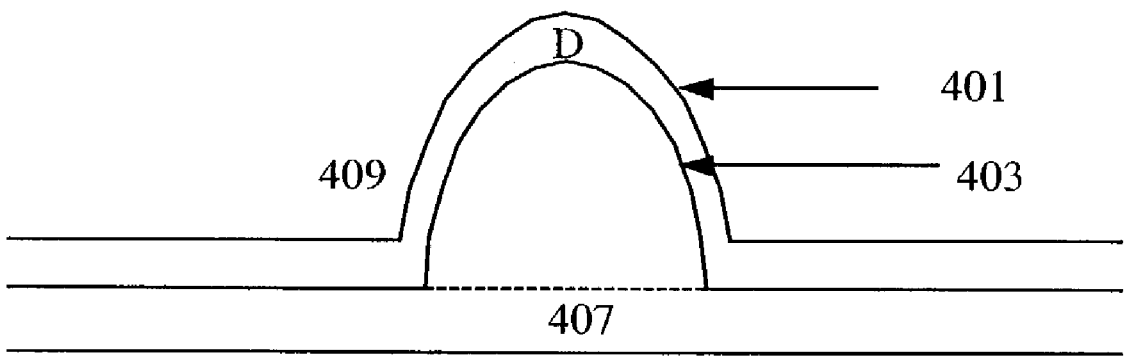
FIG. 4B is a profile model of a wafer structure comprising atmospheric gas, a top polymer material, and a bottom nitride material, in accordance to one exemplary embodiment of the present invention.

FIG. 4B illustrates an updated profile model from the profile model of FIG. 4A. The profile model comprises atmospheric gas 409, a top polymer material 401 with a thickness of D, a bottom nitride material 403, and underlying film 407. Along the line of periodicity of the structure, there are three materials consisting of the nitride material 403, the polymer material 401, and atmospheric gas 409.

Figure 5:
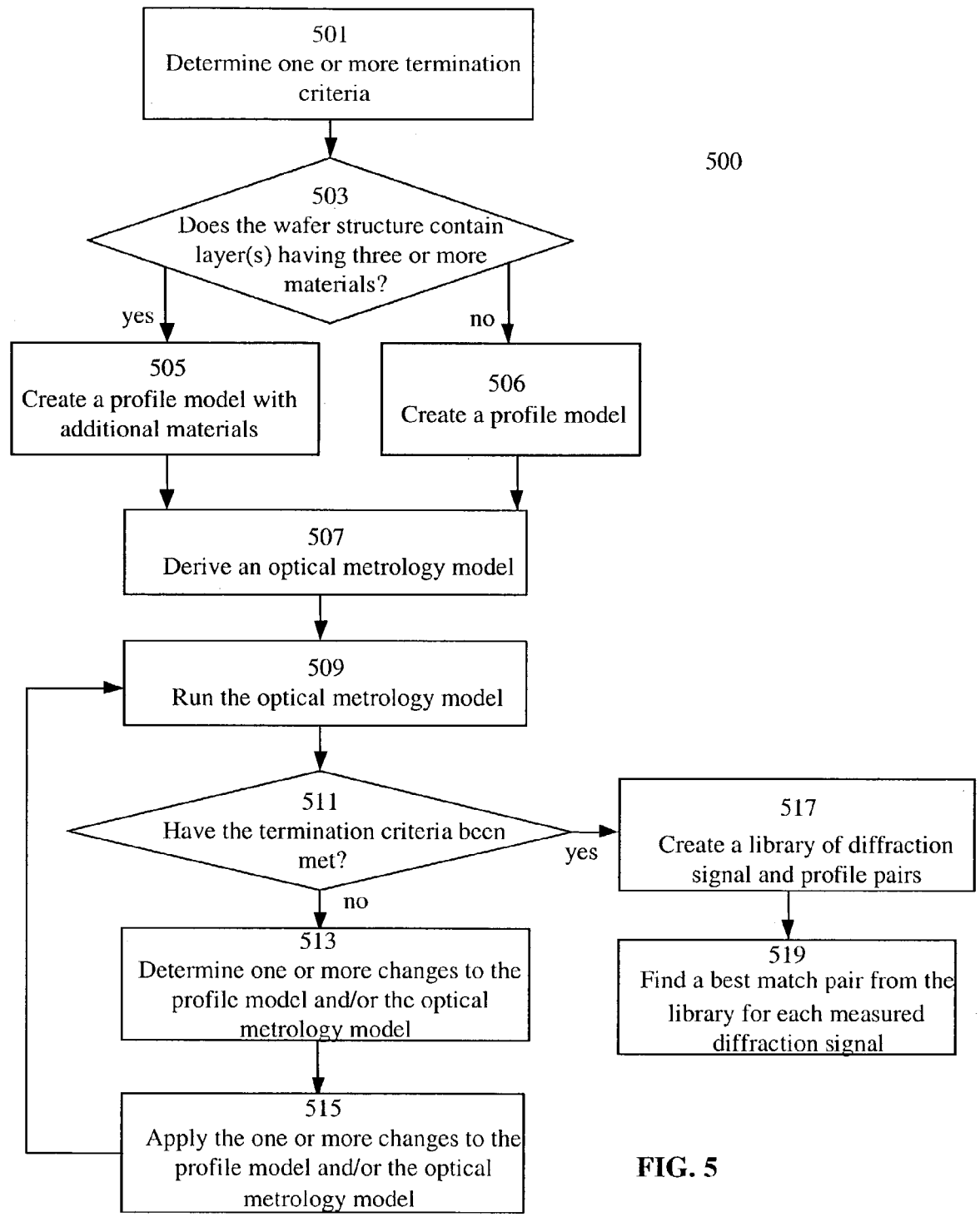
FIG. 5 is a flow chart of an exemplary process.

FIG. 5 is a flow chart 500 of an exemplary process to create an optical metrology profile model for a wafer structure according to the composition of the layers on the wafer structure.

In Step 501, one or more termination criteria are determined. For example, the termination criteria may include an acceptable cost function value of a simulated diffraction signal wherein the cost function value is based on difference of the simulated diffraction signal compared to a measured diffraction signal.

In a second exemplary embodiment, the termination criteria may be an acceptable or acceptable maximum sum-squared error (SSE) value.

In a third exemplary embodiment, the termination criteria may be a goodness-of-fit (GOF) between a measured diffraction signal and a simulated diffraction signal. Moreover, the termination criteria may include a combination of one or more termination criteria such as an acceptable maximum sum squared error value in combination with a minimum GOF value.

With reference to FIG. 5, in Step 503, one or more input parameters of the wafer structure are checked to determine if any of the one or more layers on the wafer structure comprises more than two distinct materials along a line in any of the one or more layers. For example, the input data from the customer process engineer may specify in the input parameters that the wafer structure has a polymer coating. As mentioned above, the material of the layer, the polymer coating, and atmospheric gas would comprise three materials along a line in a layer. In another example involving a previous CMP step, the input parameters may include three materials consisting of nitride, silicon dioxide, and atmospheric gas as in the structure depicted in FIG. 2. Moreover, a layer comprising three or more distinct materials along a line in the layer is considered to have additional materials, and a profile model of a wafer structure having at least one layer composed of three or more distinct materials along a line is created by incorporating the presence of the additional materials in Step 505. Alternatively, a profile model of a wafer structure that does not comprise any layer having three or more distinct materials is created without incorporating any additional material in Step 506.

A layer on a wafer structure may comprise three or more materials along a line within the layer under various circumstances including: over etching, under etching, measurement at a pre-clean stage, the presence of an un-modeled film, and the presence of a hard mask. FIG. 2, FIG. 3, and FIG. 4B are exemplary embodiments where a layer on the wafer structure comprises three or more materials along a line in the layer.

Referring now back to FIG. 5, in Step 507, an optical metrology model of the wafer structure is derived according to the profile model created in Step 505 or Step 506. For a description of wafer structure modeling, refer to co-pending U.S. patent application Ser. No. 10/206, 491, entitled "Model and Parameter Selection in Optical Metrology" by Voung, et al., filed on Jul. 25, 2002, and is incorporated in its entirety herein by reference.

In Step 509 of FIG. 5, the optical metrology model is run and invokes a diffraction signal simulation algorithm that takes into account the presence of three or more materials in one or more layers. Moreover, any additional materials incorporated in the profile model are taken into consideration in the optical metrology model by invoking an additional materials rigorous coupled-wave analysis (RCWA). For a description of incorporating three or more materials in an optical metrology model and the use of RCWA, refer to co-pending U.S. patent application Ser. No. 10/007,124, entitled "Optical Profilometry of Additional Material Deviations in a Periodic Grating", by Niu, et al., filed on Dec. 4, 2001, and is incorporated in its entirety herein by reference.

Moreover, the output data of the invoked diffraction signal simulation algorithm includes: simulated diffraction signals for the wafer structure, underlying film thickness, profile measurements, and critical dimension (CD) measurements.

In Step 511, once the optical metrology model runs completely, the simulated diffraction signals and a set of diffraction signals measured off the wafer structure are compared to determine if the one or more termination criteria are met. The measured set of diffraction signals is obtained through the use of an integrated or stand-alone optical metrology device. If the termination criteria are not met, one or more changes for the profile model and/or the optical metrology model are determined and implemented in Steps 513 and 515 respectively, and the process continues with the modified optical metrology model from Step 509.

For example, a GOF of 0.995 between the measured diffraction signals and the simulated diffractions signals may be set as the termination criteria. If the calculated GOF is equal to or greater than 0.995, i.e., the termination criteria are met, the process continues to Step 517.

Alternatively, a cost function less than 2.5 between the measured diffraction signals and the simulated diffraction signals may be used as the termination criteria. If the calculated cost function is less than 2.5, i.e., the termination criteria are met, the process continues to Step 517.

Furthermore, in a third embodiment, a GOF of 0.995 and a cost function less than 2.5 may be used in combination as the termination criteria, wherein the termination criteria are not met unless the calculated GOF is equal to or greater than 0.995 and the calculated cost function is less than 2.5.

An optical metrology model may not meet the termination criteria under various circumstances including: an overlooked layer on the wafer structure; residue on wafer due to measurements at a pre-clean stage; an un-modeled film or material. FIG. 4A and FIG. 4B illustrate an exemplary embodiment wherein an overlooked material may prevent an optical metrology model from meeting a set of one or more termination criteria.

As mentioned above, FIG. 4A illustrates a profile model comprising two distinct materials of atmospheric gas and nitride. Assume that the optical metrology model using the profile model of FIG. 4A does not meet a set of one or more termination criteria, and during the process of modification, it is discovered that a layer of polymer on the structure has been overlooked.

FIG. 4B illustrates an updated profile model from the profile model of FIG. 4A. The updated profile model includes a top polymer material 401 and a bottom nitride material 403. The optical metrology model, using the updated profile model is run and if the set of one or more termination criteria are met, then processing proceeds to Step 517 in the flow chart illustrated in FIG. 5.

In an alternative example, assume that the profile model shown in FIG. 4B does not meet a set of one or more termination criteria. The optical metrology model is based on the thickness of the polymer material 401 denoted D. Moreover, the thickness D is given as a range greater than or equal to 5 nanometers (nm) and less than or equal to 10 nm. In one exemplary embodiment, the thickness D is modified to be greater than or equal to 2 nm and less than or equal to 15 nm in order to meet the one or more termination criteria.

Referring now back to FIG. 5, assume in Step 511 that the termination criteria are met. In Step 517, a library of simulated diffraction signal and profile pairs is created according to profile parameters, and resolution of the profile parameters of the optical metrology model. A method of library generation of grating profiles is described in co-pending U.S. patent application Ser. No. 09/727,530 entitled "System and Method for Real-Time Library Generation of Grating Profiles" by Jakatdar, et al., filed on Nov. 28, 2000, and is incorporated in its entirety herein by reference.

In Step 519, each of the measured diffraction signals is compared to the diffraction signal and profile pairs in the library, and one diffraction signal and profile pair, also known as a best match, is selected from the library for each measured diffraction signal according to criteria such as GOF. For a description of best matching a measured diffraction signal to a simulated diffraction signal and profile pair in a library, refer to co-pending U.S. patent application Ser. No. 09/727,530, entitled "System and Method for Real-Time Library Generation of Grating Profiles" by Jakatdar, et al., filed on Nov. 28, 2000, and is incorporated in its entirety herein by reference.

Moreover, data extracted from the best match diffraction signal and profile pairs in Step 519 may be used as feedback data to the lithography control system (not shown) to adjust process parameters of previous fabrication processes or used as feed-forward data to adjust process parameters of later fabrication processes.

Figure 6:
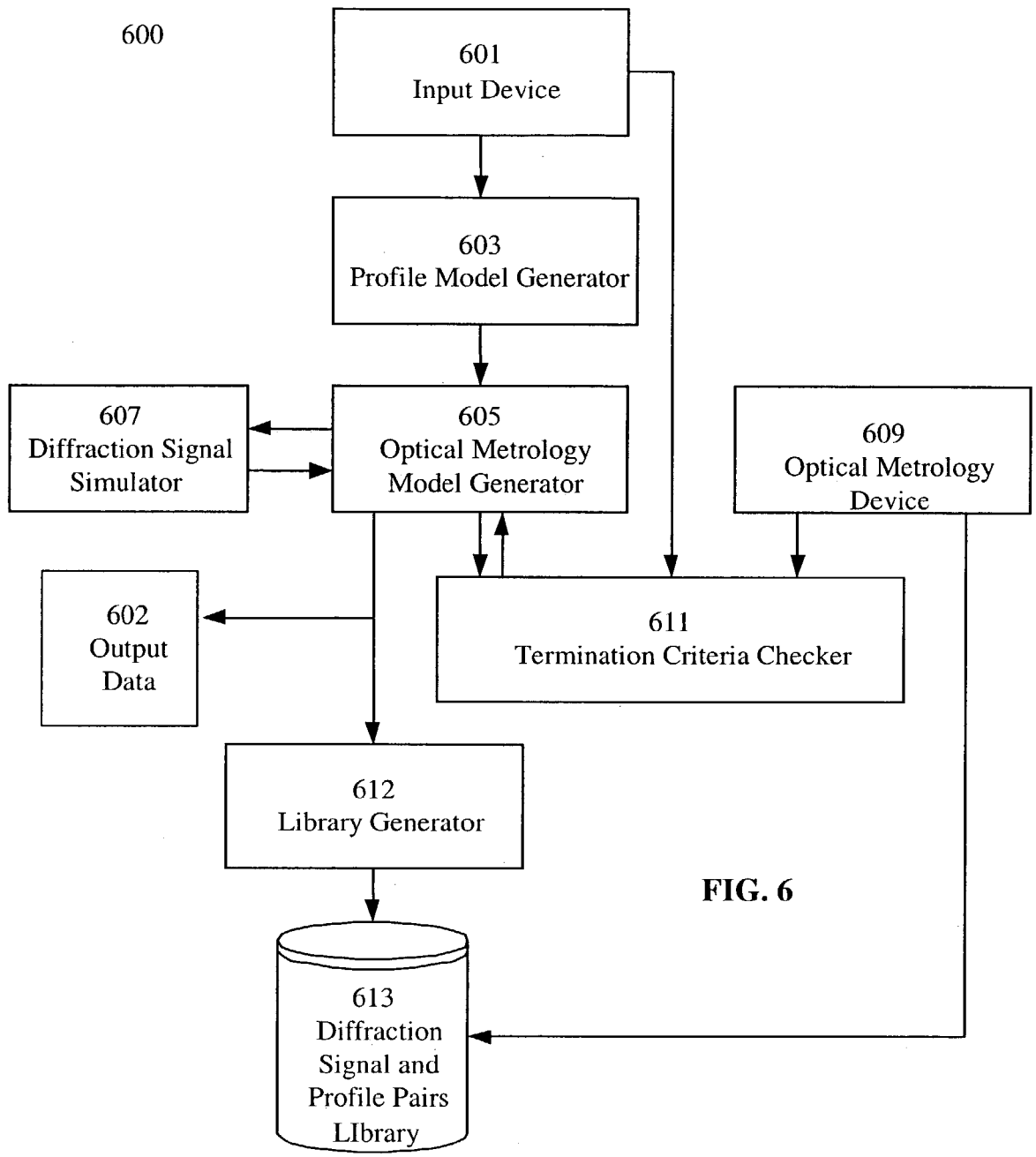
FIG. 6 is an exemplary system flow.

FIG. 6 is a system flow diagram 600 of a system for modeling wafer structure with additional materials according to one embodiment of the present invention. An input device 601 transmits information including wafer structure composition data and termination criteria to a profile model generator 603. Profile model generator 603 generates profile models that incorporate the presence of additional material given a wafer structure comprising at least one layer having three or more distinct materials in the layer. Profile model generator 603 transmits generated profile models to optical metrology model generator 605 in order to derive optical metrology models. Optical model generator 605 in turn invokes a diffraction signals simulation algorithm in a diffraction signal simulator 607 to simulate a set of diffraction signals for the optical metrology models.

Moreover, the invoked simulation algorithm incorporates possible presence of additional materials into the generated optical models by incorporating RCWA. For a description of incorporating three or more materials in an optical metrology model and the use of RCWA, refer to co-pending U.S. patent application Ser. No. 10/007,124, entitled "Optical Profilometry of Additional Material Deviations in a Periodic Grating", by Niu, et al., filed on Dec. 4, 2001, and is incorporated in its entirety herein by reference.

Diffraction signal simulator 607 outputs simulated diffraction signals and transmits the simulated signals back to optical metrology model generator 605. Optical metrology model generator 605 receives the simulated signals from simulator 607; generates output data including underlying film thickness, profile measurements, and critical dimension measurements; and transmits the output data to a termination criteria checker 611. An optical metrology device 609 obtains diffraction signals off the wafer structure and transmits the signals to termination criteria checker 611. Termination criteria check 611 receives a set of one or more termination criteria from input device 601 and checks if the one or more termination criteria are met according to data received from optical metrology model generator 605 and optical metrology device 609. If the termination criteria are met, a signal is sent to optical metrology model generator 605 and output data 602 from optical metrology model generator 605 are transmitted to a library generator 612 in order to generate a library 613 comprising diffraction signal and profile pairs. Optical metrology device 609 transmits the obtained diffraction signals to library 613. Each of the obtained diffraction signals is compared to diffraction signal and profile pairs in library 613, and for each obtained diffraction signal, a diffraction signal and profile pair, also known as a best match, is selected according to criteria such as GOF.

Figure 7:
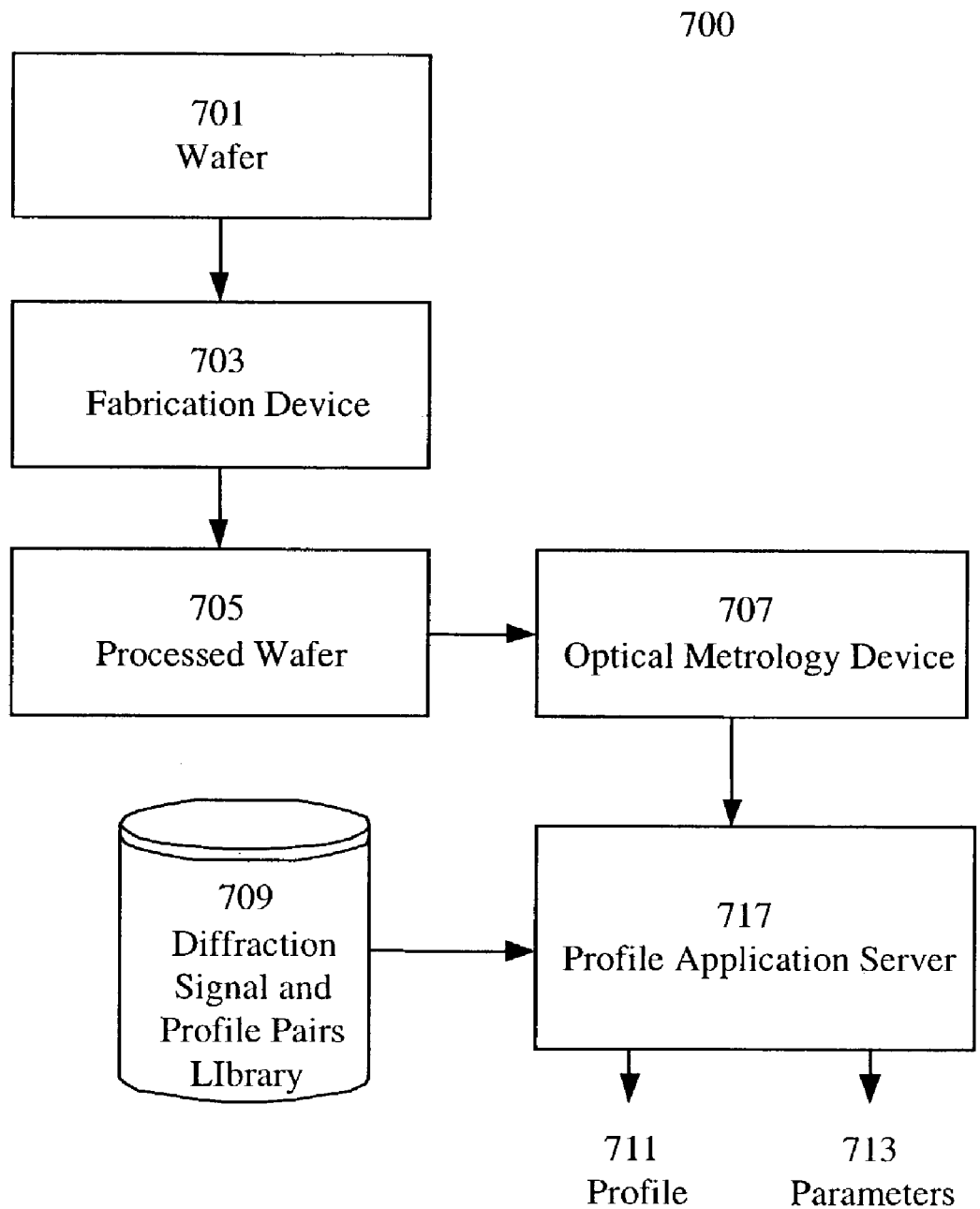
FIG. 7 is another exemplary system flow.

FIG. 7 is a system flow diagram 700 of a system for monitoring and correcting lithographic processes. An unprocessed wafer 701 is processed in a lithographic step (e.g., resist coating, developing, etching, etc.) by a fabrication device 703. An optical metrology device 707 measures diffraction signals off target structures on processed wafer 705 and transmits the measured diffraction signals to a diffraction signal and profile pairs library 709. Moreover, library 709 is incorporated in a profile application server 717 and generated according to an optical metrology model such as library 613 in FIG. 6. The measured diffraction signals from optical metrology device 707 are compared to the diffraction signal and profile pairs in library 709 incorporated in profile application server 717 and for each measured diffraction signal, a pair of diffraction signal and profile pair is selected from library 709 according to criteria such as GOF. The selected profiles 711 and associated parameters 713 are then compared to acceptable ranges of the profiles 711 and associated parameters 713 in order to detect process defects such as over etching or under etching. Moreover, the comparison results may be used as feedback data to the lithography control system (not shown) to adjust process parameters of previous fabrication processes or used as feed-forward data to adjust process parameters of later fabrication processes.

It is contemplated that functional implementation of the present invention described herein may be implemented equivalently in hardware, software, firmware, and/or other available functional components or building blocks.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the arts to best utilize the invention and various embodiments with various modifications as are suited to the particular use contemplated. It is intended that the scope of the invention be defined by the Claims appended hereto and their equivalents.

For example, although a layer comprising three or more distinct materials in the layer is described above as having additional materials, the threshold may be set higher or lower. In an alternative embodiment, only layers comprising four or more distinct materials in a line within the layer are considered to have additional materials.

We claim:

1. A method of modeling wafer structure profile, the method comprising:
    a) determining one or more termination criteria;
    b) determining whether a wafer structure includes at least one layer having three or more materials along a line within the at least one layer;
    c) creating an optical metrology model, wherein three or more materials are incorporated in the model of the at least one layer having three or more materials;
    d) obtaining a set of diffraction signals converted from a set of diffraction beams measured off of the wafer;
    e) simulating a set of diffraction signals using the optical metrology model;
    f) determining if the one or more termination criteria are met by using the set of simulated diffraction signals and the set of diffraction signals converted from the set of diffraction beams measured off of the wafer; and
    g) if the one or more termination criteria are not met, modifying the optical metrology model and repeating steps e) and f) until the one or more termination criteria are met.

2. The method of claim 1, wherein the one or more termination criteria comprises:
    testing if a cost function value of the simulated diffraction signal compared to the measured diffraction signal is less than a first cost function value.

3. The method of claim 1, wherein the one or more termination criteria comprises:

testing if a goodness of fit value of the simulated diffraction signal compared to the measured diffraction signal is greater than a first goodness of fit value.

4. The method of claim 1, wherein the one or more termination criteria comprises:
   testing if a sum-squared error value of the simulated diffraction signal compared to the measured diffraction signal is less than a first sum-squared error value.

5. The method of claim 1, wherein creating an optical model comprises:
   using rigorous coupled-wave analysis to model the layer using three or more materials.

6. The method of claim 1, wherein the wafer structure is a periodic structure having a periodic direction, and wherein the line within the at least one layer is parallel to the periodic direction.

7. The method of claim 1, wherein the set of measured diffraction signals is obtained by measuring target structures on the wafer with an optical metrology device.

8. A method of modeling wafer structure profile, the method comprising:
   a) determining one or more termination criteria;
   b) determining whether the wafer structure includes a layer having three or more materials along a line with the layer;
   c) creating an optical metrology model, wherein three or more materials are incorporated in the model for the layer having three or more materials;
   d) obtaining a set of diffraction signals converted from a set of diffraction beams measured off of the wafer;
   e) simulating a set of diffraction signals using the optical metrology model;
   f) determining if the one or mom termination criteria are met by using the set of simulated diffraction signals and the set of diffraction signals converted from the set of diffraction beams measured off of the wafer; and
   g) if the one or more termination criteria are not met:
      modifying the optical metrology model; and
      iterating steps e) and f) until the one or more termination criteria are met; and
   h) creating a library comprising diffraction signal and profile pairs according to data generated from the optical metrology model.

9. The method of claim 8, wherein the one or more termination criteria comprises:
   testing if a cost function value of the simulated diffraction signal compared to the measured diffraction signal is less than a first cost function value.

10. The method of claim 8, wherein the one or more termination criteria comprises:
    testing if a goodness of fit value of the simulated diffraction signal compared to the measured diffraction signal is greater than a first goodness of fit value.

11. The method of claim 8, wherein the one or more termination criteria comprises:
    testing if a sum-squared error value of the simulated diffraction signal compared to the measured diffraction signal is less than a first sum-squared error value.

12. The method of claim 8, wherein the creating an optical metrology model comprises:
    creating a profile model for the wafer structure by incorporating the presence of additional materials for a layer with three or more materials.

13. The method of claim 12, wherein the one or more termination criteria are not met, further comprising:
    determining one or more modifications to the profile model and/or the optical metrology model; and
    modifying the profile model and/or the optical metrology model.

14. The method of claim 8, further comprising:
    creating a profile model for the wafer structure without incorporating the presence of additional materials for a layer with one or two materials.

15. The method of claim 14, wherein the one or more termination criteria are not met, further comprising:
    determining one or more modifications to the profile model and/or the optical metrology model; and
    modifying the profile modal and/or the optical metrology model.

16. The method of claim 8, wherein the set of measured diffraction signals is obtained by measuring target structures on the wafer with an optical metrology device.

17. The method of claim 8, further comprising:
    comparing each of the set of one or more measured diffraction signals to the diffraction signal and profile pairs library; and
    selecting a best match diffraction signal and profile pair from the library for each of the measure diffraction signals.

18. A computer-readable storage medium containing computer executable code to create an optical metrology model for a wafer structure by instruction the computer to operate as follows:
    a) determining one or more termination criteria;
    b) determining whether the wafer structure includes at least one layer having three or more materials along a line within the at least one layer;
    c) creating an optical metrology model, wherein three or more materials are incorporated in the model for the at least one layer having three or more material;
    d) obtaining a set of diffraction signals converted from a set of diffraction beams measured off of the wafer;
    e) simulating a set of diffraction signals using the optical metrology model;
    f) determining if the one or more termination criteria are met by using the set of simulated diffraction signals and ate set of diffraction signals converted from the set of diffraction beams measured off of the wafer; and
    g) if the one or more termination criteria are not met:
       modifying the optical metrology model; and
       iterating steps e) and f) until the one or more termination criteria are met.

19. The computer-readable storage medium of claim 18, wherein the set of measured diffraction signals is obtained by measuring target structures on to wafer with an optical metrology device.

20. A system for creating an optical metrology model for a wafer structure, the system comprising:
    an input device configured to transmit a set of wafer composition data;
    a profile model generator configured to received the set of wafer composition data from the input device and generate a profile model of the wafer structure, wherein the profile model incorporates to presence of additional materials for a wafer comprising at least one layer having three or more materials along a line within the at least one layer;
    an optical metrology model generator coupled to the profile model generator, wherein the optical metrology model is configured to receive the profile model from the profile model generator and generate an optical metrology model according to the profile model and a set of model output data;

a diffraction signal simulator coupled to the optical metrology model generator, wherein the diffraction signal simulator is configured to generate a set of simulated diffraction signal;

an optical metrology device configured to measure a set of diffraction beams off the wafer structure and convert the diffraction beams into a set of diffraction signals; and a termination criteria checker coupled to the input device, the diffraction signal simulator, and the optical metrology device, wherein to termination criteria checker is configured to receive the one or more termination criteria from the input device, the set of simulated diffraction signals from the diffraction signal simulator, and the set of diffraction signals converted from the set of diffraction beams measured off the wafer structure from the optical metrology device, and wherein the termination criteria checker is configured to determine if the one or more termination criteria are met using the set of simulated diffraction signals and the set of diffraction signals measured off of the wafer.

21. The system of claim 20, wherein the input device is further configured to transmit a set of one or more termination criteria.

22. The system of claim 21, wherein the set of model output data includes profile, CD measurements, and underlying film thickness.

23. The system of claim 20, wherein the optical metrology system includes an ellipsometer or a reflectometer.

24. The system of claim 20, wherein the optical metrology model generator is further configured to incorporate the effect of three or more materials in the simulated diffraction signals.

25. A system for generating a diffraction signal and profile pairs library by creating an optical metrology model, the system comprising:

an input device configured to transmit a set of wafer composition data;

a profile model generator configured to received the set of wafer composition data from the input device and generate a profile model of the wafer structure, wherein the profile model incorporates the presence of additional materials for a layer of the wafer structure having three or materials along a line in the layer;

an optical metrology model generator coupled to the profile model generator, wherein the optical metrology model is configured to receive the profile model from the profile model generator, generate an optical metrology model according to the profile model;

a diffraction signal simulator coupled, to the optical metrology model generator, wherein the diffraction signal simulator is configured to generate a set of simulated diffraction signals; and a library generator coupled to the optical metrology generator, the library generator configured to generate a library of diffraction signal and profile pairs;

an optical metrology device configured to measure a set of diffraction beams off the wafer structure and convert the set of diffraction beams into a set of diffraction signals; and a termination criteria checker coupled to the input device, the diffraction signal simulator, and the optical metrology device, wherein the termination criteria checker is configured to receive the one or more termination criteria from the input device, the set of simulated diffraction signals from the diffraction signal simulator, and the set of diffraction signals converted from the set of diffraction beams measured off the wafer structure from the optical metrology device, and wherein the termination criteria checker is configured to determine if the one or more termination criteria are met using the set of simulated diffraction signals and the set of diffraction signals measured off of the wafer.

26. The system of claim 25, wherein the input device is further configured to transmit a set of one or more termination criteria.

27. The system of claim 26, wherein the optical metrology model is generated according to a set of model output data including profile, CD measurements, and underlying film thickness.

28. The system of claim 25, wherein the optical metrology system includes an ellipsometer or a reflectometer.

29. The system of claim 25, wherein the optical metrology model generator further comprises:

a rigorous coupled-wave analysis process unit for incorporating additional materials in the generated optical metrology model.

30. A system for monitoring and correcting a lithographic process, the system comprising:

an optical metrology device configured to measure diffraction beams off a wafer structure and convert them to diffraction signals;

an optical metrology model generator configured to generate an optical metrology model;

a diffraction signal simulator coupled to the optical metrology model generator, wherein the diffraction signal simulator is configured to generate a set of simulated diffraction signals;

a termination criteria checker coupled to the diffraction signal simulator and the optical metrology device, and wherein the termination criteria checker is configured to determine if one or more termination criteria are met using the set of simulated diffraction signals and the set of diffraction signals converted from the set of diffraction beams measured off of the wafer; and a profile application server coupled to the optical metrology device, wherein the profile application server further comprises:

a diffraction signal and profile pairs library, the library created with an optical metrology model, wherein the optical metrology model is created by incorporating additional materials for wafer structures having at least one layer with three or more materials along a line with the at least one layer.

31. The system of claim 30, wherein the library is configured to received the diffraction signals from the optical metrology device.

32. The system of claim 30, wherein the optical metrology system includes an ellipsometer or a reflectometer.

* * * * *